United States Patent [19]

Sandler

[11] Patent Number: 5,015,776
[45] Date of Patent: May 14, 1991

[54] PREPARATION OF 3-(ALKYLTHIO) ALDEHYDES

[75] Inventor: Stanley R. Sandler, Springfield, Pa.

[73] Assignee: Atochem North America, Inc., Philadelphia, Pa.

[21] Appl. No.: 483,343

[22] Filed: Feb. 20, 1990

Related U.S. Application Data

[63] Continuation of Ser. No. 330,560, Mar. 30, 1989, abandoned, which is a continuation of Ser. No. 924,077, Oct. 28, 1986, abandoned.

[51] Int. Cl.$^5$ ............................................. C07C 319/00
[52] U.S. Cl. ...................................................... 568/41
[58] Field of Search ........................................... 568/41

[56] References Cited

U.S. PATENT DOCUMENTS 3,529,940  9/1970  Shima et al. ........................... 568/41
4,036,751  7/1977  Orita et al. ............................ 210/35

FOREIGN PATENT DOCUMENTS 27-6380   12/1954  Japan ..................................... 568/41
40-19090   8/1965  Japan ..................................... 568/41
1336541   11/1973  United Kingdom ................... 568/41

OTHER PUBLICATIONS

Yamada et al., "Applications of Ion Exchange Resins in Organic Reactions", Jour. of Pharm. Soc., Japan (1953) (Translation copy only).

Szabo et al., "Reactions of Mercaptans with Unsaturated Compounds", Jour. Amer. Chem. Soc., 70, 3667 (1948).

Hall et al., "Reactions of Crotonaldehyde with Ethanethiol", Jour. Chem. Soc., 2723 (1949).

Wheaton et al., "Ion Exchange" Ency. of Chem. Tech. (Kirk-Othmer), Wiley, 2nd Ed., vol. 11 (1966).

Primary Examiner—Bruce Gray

[57] ABSTRACT

A process for preparing 3-($C_1$–$C_{12}$ alkylthio) $C_3$–$C_{10}$ aldehydes by reacting a $C_1$–$C_{12}$ alkyl mercaptan with an $\alpha,\beta$-unsaturated aliphatic aldehyde having from 3 to 10 carbon atoms in the presence of a weakly basic exchange resin having polyamine functionality and being in the free base form, is disclosed herein.

6 Claims, No Drawings

PREPARATION OF 3-(ALKYLTHIO) ALDEHYDES

This is a continuation of copending application Ser. No. 0/330,560 filed on Mar. 30, 1989 now abandoned * which is a continuation of abandoned application Ser. No. 924,077 filed Oct. 28, 1986.

BACKGROUND OF THE INVENTION

This invention relates to the facile preparation of 3-(alkylthio)aldehydes by the reaction of a $C_1$–$C_{12}$ alkyl mercaptan with a $C_3$–$C_{10}$ unsaturated aliphatic aldehyde in the presence of a specified exchange resin catalyst. More particularly, this invention relates to the preparation of 3-($C_1$–$C_{12}$ alkylthio) $C_3$–$C_{10}$ alkanals in the presence of a catalytic amount of weakly basic and exchange resin having polyamine functionality and being in the free base form.

The products of the process of this invention have various uses including, for example, intermediates for the preparation of pesticides and antioxidants and as odorant or flavoring agents.

Prior Art

It is known to prepare 3-(alkylthio) propional by the reaction of a lower alkyl mercaptan and acrolein in the presence of a strongly basic anion exchange resin in the hydroxide ($OH^-$) form or where the hydroxide groups are replaced with cyanide ($CN^-$) ions [Japanese Patent Application No. 27-6380 and Yamada et al., "Application of Ion Exchange Resins in Organic Reactions", J. of Pharm. Soc., Japan (1953)]. Weakly basic anionic ion exchange resins which are condensation products of primary to tertiary amines with phenol formaldehyde or the like and in the hydroxide form are also said to be useful catalysts. The use of resins as catalysts in the free base form are not mentioned.

Triethylamine and other basic catalysts have also been reported as used for the reaction of lower alkyl mercaptans with $\alpha$, $\beta$-unsaturated aliphatic aldehydes [Hall, R. H. et al., J Chem. Soc., 2723 (1949) and U. K. Patent Spec. No. 1,336,541.

The prior art catalyst containing the hydroxide functionality suffers from the disadvantage of producing high boiling or polymeric products. Szabo, J. L. et al. [J. Amer. Chem. Soc., 70, 3667 (1948) "Reaction of Mercaptans with unsaturated Compounds"] using benzyltrimethylammonium hydroxide (Triton B), produced a high boiling product when reacting crotonaldehyde with ethyl mercaptan (see No. 13 of Table I in the footnote reference), which is not their reported $\beta$-(ethylthio)butyraldehyde [same as 3-(ethylthio)butanal]. Hall et al., agree with this conclusion and state on line 6 of their paper "The physical constants (b.p. 160°–180°/2 mm., $n_D^{27}1.5291$) recorded for the compound by these authors, however, appear to be in error [by comparison with those recorded in the literature for closely related compounds, e.g., 3-(ethylthio)propanal] or, more probably, the product isolated was really a polymer of the desired aldehyde." The catalysts of the present invention have the advantage of being reusable and that the product does not contain any significant amounts of high boiling components or non-volatiles.

STATEMENT OF THE INVENTION

The present invention is a process for the preparation of 3-(alkylthio)aldehydes by the reaction at a temperature within the range of about 0° to about 100° C. of a $C_1$–$C_{12}$ alkyl mercaptan with a $C_3$–$C_{10}$ $\alpha,\beta$-unsaturated aliphatic aldehyde in the presence of a weakly basic exchange resin having polyamine functionality and being in the free base form.

DETAILED DESCRIPTION OF THE INVENTION

The process of this invention represents an unexpected improvement in the preparation of 3-($C_1$–$C_{12}$ alkylthio) $C_3$–$C_{10}$ aldehydes. More preferably, it involves the preparation of 3-($C_1$–$C_6$ alkylthio)$C_3$–$C_6$ alkanals from the corresponding alkyl mercaptans and $\alpha,\beta$-unsaturated aldehydes. The alkyl groups of the mercaptans of the process include, for example, methyl, ethyl, propyl, butyl, pentyl, hexyl, heptyl, octyl, nonyl, decyl, undecyl, dodecyl and isomeric forms thereof. In addition, the alkyl groups include cycloalkyls including, for example, cyclopentyl, cyclohexyl, cycloheptyl, cycloctyl and the like. The $C_3$–$C_{10}$ aliphatic aldehydes are $\alpha,\beta$-unsaturated aldehydes and include, for example, acrolein, crotonaldehyde, pentenal, hexenal, heptenal, 2-methyl-2-pentenal, octenal, 2-methyl-2-hexenal, nonenal, and decenal. The preferred mercaptans are the $C_1$–$C_3$ alkyl mercaptans and the preferred aldehydes are the $C_3$–$C_6$ $\alpha,\beta$-unsaturated aldehydes.

The temperature at which the reaction is carried out ranges from about 0° to about 100° C., preferably from about 25° to 100° C. and more preferably from about 50° to 80° C. The pressure ranges from 1 to 50 atmospheres and preferably from 1 to 20 atmospheres. The process may be carried out in the liquid phase or in the vapor phase depending on the temperature and/or pressure employed.

The ratio of the reactants in the process reaction generally ranges from about 1:1 to about 1:3 and is preferably at about 1:1 to about 1:1.5 moles of alkyl mercaptan per mole of unsaturated aldehyde.

The use of a solvent is optional for the reaction but may be employed, particularly when the reaction is carried out with higher alkyl compounds. Suitable solvents are, for example, tetrahydrofuran, dioxane and water.

The critical feature of the present invention is in the use as a catalyst of a weakly basic ion exchange resin having polyamine functionality and being in the free base form. The matrix resin for the catalyst material can be, for example, methacrylic/divinylbenzene, acrylic/divinylbenzene, styrene/divinylbenzene, styrene/divinylbenzene/acrylic and the like, such resins being crosslinked to various degrees through crosslinking agents or copolymer components (eg. divinylbenzene) which have substituent groups which react with one-another across the polymer chains. The preferred matrix resins are those which provide microporous or macroreticular structures and are in bead form. The preferred macroreticular catalysts comprise resin matrixes wherein the polyamine functionality has pendant tertiary amine groups. An example of this type of preferred catalyst, which can be obtained from Rohm & Haas Company, is the product designated Amberlyst ® A21. Other such catalysts for this invention which are commercially available are the Rohm & Haas Company products designated Amberlite ® IRA35, IRA45, IRA47S, IRA60, IRA68, and IRA93.

The resin catalyst is used in varying amounts in the process depending upon the mode of operation. In batch operations, the catalyst is preferably stirred with the reactants using 1 to 50 grams of catalyst per mole of either reactant. A preferred range is 1 to 20 grams per mole of either reactant. In a continuous operation, a catalyst bed is used in which the reactants, either in liquid or vapor phase, are passed over the catalyst preferably at a molar velocity ranging between about 100 to about 4000 gram-moles of mercaptan per kilogram of catalyst per 24 hours. In the continuous mode of operation, the catalyst bed may be of various lengths with sufficient catalyst exposure to give high conversion rates per pass. The unreacted compounds are removed and recycled with sufficient make-up reactants to provide the appropriate ratio of mercaptan to aldehyde.

EXAMPLES

The following examples illustrate this invention. Gas chromatography was used to determine the purity of the (alkylthio)aldehyde prepared.

EXAMPLE 1

To a reactor equipped with a mechanical stirrer, addition funnel, condenser and thermometer was added 85.5 g (1.22 mole) of anhydrous crotonaldehyde and 16.3 g Amberlyst ® A-21 (as-is condition from Rohm & Haas). The mixture was stirred and heated to 50° C. while 77.1 g (1.24 mole) of ethyl mercaptan was added drop wise. The reaction was exothermic and cooling was necessary in order to keep the temperature throughout at 50°-55° C. The mixture was stirred for an additional 4 hours at 70°-75° C., cooled and the gas chromatographic analysis at this point indicated a 90% conversion to 3-(ethylthio)butanal. The unreacted starting materials are removed by heating under reduced pressure and can be reused in subsequent preparations.

EXAMPLE 2

Unused Amberlyst ® A-21 catalyst is first washed with distilled water and methanol solution as described below before being used to prepare 3-(ethylthio)butanal. 178.0 g of the catalyst is washed successively twice at room temperature with each of 200 g water, 200 g 33% aqueous methanol (by volume), and 200 g methanol. Then the catalyst was dried under reduced pressure at 50° C. to constant weight.

13.5 g of the drried catalyst was added to 273 g (3.9 moles) of crotonaldehyde in the reactor described in Example 1, and the mixture stirred and heated at 60° C. by means of a water bath. Then ethyl mercaptan was added portion wise in about 25 minutes until 230 g (3.7 moles) was added. The temperature in the flask rose from 35° C. to 78° C. during the addition period. A gas chromatographic analysis at this point indicated an 88% conversion to product. Heating was continued at 80° C. for 2.5 hours then cooled and the product decanted from the resin catalyst. A gas chromatographic analysis of the crude indicated that it contained 94% of 3-(ethylthio)butanal. The unreacted starting materials are removed under reduced pressure and can be reused in subsequent preparations. This example indicates that there is a slight advantage in using a washed catalyst.

The catalyst recovered from the above procedure was used again to prepare 3-(ethylthio)butanal in the procedure described above in this example to give similar results.

EXAMPLE 3

Crotonaldehyde and ethyl mercaptan are fed into a catalytic bed of Amberlyst ® A-21 which was kept at 50° C. at such a rate to keep the mole ratio of each approximately 1:1. The unreacted materials are recovered and recycled and the product 3-(ethylthio)butanal is obtained as a stripped crude or a distilled product.

EXAMPLE 4

Crotonaldehyde, nitrogen and ethyl mercaptan are brought together in an adequate mixing device and thoroughly mixed prior to being fed into a packed-bed containing a mixture of Amberlyst ® A-21 and glass beads which are kept at a temperature above 50° C. The crotonaldehyde and ethyl mercaptan feed rates were controlled by rotometers to keep the mole ratio at about 1:1. The product stream was monitored by gas chromatography. The liquid product is separated from the unreacted starting materials which are recovered for reuse.

The catalysts of this invention provide superior results for the process of preparing 3-(alkylthio)aldehydes from mercaptans and unsaturated aldehydes since they provide products with low non-volatile content. The prior art process of preparing the alkylthioaldehydes, eg. 3-(ethylthio)propanal, utilizing the anion exchange resin in the hydroxide form (Amberlite ® IRA 400) is not suitable for preparing, for example, 3-(ethylthio)-butanal, since the product will have a high non-volatile content (or polymers).

The catalysts of this invention, compared to other basic catalyst known for this reaction, are reusable and non-contaminating to the product because they can be easily separated by simple filtration or decantation. They can also be packed in columns which make these resin catalysts suitable for continuous operation. Triethylamine, on the other hand, is difficult to remove from the product causing a decrease in storage stability.

I claim:

1. A process for the preparation of 3-(alkylthio) butanal which comprises reacting at a temperature within the range of about 25° to 100° C. a $C_1$-$C_6$ alkyl mercaptan with crotonaldehyde in the presence of a polyamine functionality and being in the free base form.

2. The process of claim 1, wherein the polyamine functionality of the exchange resin has pendant tertiary amine groups. .

3. The process of claim 1, wherein the exchange resin is macroreticular.

4. The process of claim 1, wherein the process is carried out in the vapor phase.

5. The process of claim 1, wherein the process is carried out in the liquid phase.

6. The process of claim 1, wherein the alkyl mercaptan is ethyl mercaptan.

* * * * *